(12) United States Patent
Madanshetty

(10) Patent No.: US 6,981,408 B1
(45) Date of Patent: Jan. 3, 2006

(54) THIN-FILM ADHESION TESTING METHOD AND APPARATUS

(76) Inventor: Sameer I. Madanshetty, 6923 Redbud Dr., Manhattan, KS (US) 68503

(*) Notice: Subject to any disclaimer, the term of this patent is extended or adjusted under 35 U.S.C. 154(b) by 0 days.

(21) Appl. No.: 10/804,126

(22) Filed: Mar. 19, 2004

Related U.S. Application Data

(60) Provisional application No. 60/455,577, filed on Mar. 19, 2003.

(51) Int. Cl.
*G01N 17/00* (2006.01)
(52) U.S. Cl. .................................. 73/150 A
(58) Field of Classification Search .............. 73/150 A
See application file for complete search history.

(56) References Cited

U.S. PATENT DOCUMENTS 4,501,768 A * 2/1985 Kumar ....................... 427/560
5,045,007 A * 9/1991 Edwards et al. ............... 445/2
6,604,420 B2 * 8/2003 Hawbaker et al. ............ 73/588

* cited by examiner

*Primary Examiner*—Charles Garber
(74) *Attorney, Agent, or Firm*—McIntyre Harbin & King, LLP

(57) ABSTRACT

A method of testing thin film adhesion includes placing the film at the focus of a cavitation-producing sound beam. Time required to achieve spot erosion provide a measure of adhesion strength. No erosion occurs when insonification pressure amplitude remains below a threshold value. At pressures above a threshold value, cavitation intensity increases with pressure and erosion time decreases. A plot of erosion time versus pressure amplitude reveals a decreasing time versus insonification pressure. The intercept of the plot with the pressure axis corresponds to the instantaneous erosion of the thin film, and thus the adhesion strength. Further, the threshold value of the pressure at which no erosion occurs indicates infinite life of the thin film under cyclic loading and thus corresponds to the endurance limit, i.e., the fatigue strength, of the thin film. A corresponding apparatus is also disclosed.

3 Claims, 2 Drawing Sheets

THIN-FILM ADHESION TESTING METHOD AND APPARATUS

CROSS-REFERENCE TO RELATED APPLICATION

This application claims the benefit of Provisional Application Ser. No. 60/455,577 filed Mar. 19, 2003 in the name of the same inventor hereof.

BACKGROUND

This invention relates to testing adhesion of a thin film on a substrate.

Thin surface coatings are deposited in various ways and serve diverse purposes such as providing resistance to wear and corrosion, reducing friction, providing specialized optical properties, or to obtain desirable electrical or magnetic attributes. It is desired to adequately bond the thin film to its substrate in order to accomplish their design intent. Adhesion between the film and its base material is the limiting factor to operational usefulness. For example, diamond thin films are very hard but its adhesion to steel is limited due to the interfacial adhesion. Similarly, cubic-BN is nearly as hard as diamond but the hexagonal-BN phase that forms as the initial substrate-film interface has very poor adhesion.

Adhesion is a function of interfacial bond strength and a host of other factors. The force or the work required to detach in situ a given thin film coating from its substrate indicates adhesion strength. In The Materials Science of Thin Films, Milton Ohring (1992), "ASTM defines adhesion as the condition in which two surfaces are held together by valance forces or by mechanical anchoring or by both together." Adhesion to a substrate is the first attribute a film must possess before any of its other properties can be successfully exploited. The lack of a broadly applicable method for quantitatively measuring adhesion makes it virtually impossible to test the efficacy of prior techniques. The ACIM method of assessing thin film integrity is expected to fulfill this requirement.

Several methods are currently used to indirectly measure thin film adhesion. These include the scratch test, peel test, and indentation test. In the scratch test, a smooth but finely pointed stylus is drawn across the film under increasing vertical loads. The critical load required to strip the film from its substrate and leave a clear channel indicates adhesion strength. In the peel test, thin film adhesion is measured by the tensile force required to pull the film directly from its substrate. In the peel test or the tape test, adhesive tape is pressed onto the thin film and then torn off. The quality of adhesion is judged by whether the film is pulled off with the tape. In the indentation test, which can be called an impression test, forces imposed through an indentation to introduce a residual stress field that causes the interface to delaminate. Based on the measurements of the force and the size of the induced delamination one can estimate the interface toughness. Impression tests are typically used on ductile substrates having well established stress/strain characteristics. Other specialized tests include the bulge test and the blister test, which require very special sample preparations. Nano indenting is a new method for characterizing mechanical properties on micro-scale-features less than 100 nm across and thin films less than five nm thick.

SUMMARY OF THE INVENTION

In accordance with a first aspect of the present invention, there is provided a method of testing adherence of a thin film on a substrate comprising subjecting the thin film to the insonification pressure, producing microcavitation energy to bring about cavitation, plotting erosion time of the thin film versus insonification pressure level, and determining an instantaneous erosion pressure based on the plotting. The plotting is preferably based on elapse time to observe a spot erosion of the thin film to expose the underlying substrate. In another aspect of the invention, an instantaneous erosion pressure is determined by extrapolating the plot of erosion time per unit area versus pressure to the pressure axis.

In accordance with another aspect of the invention, there is provided a method of determining the endurance limit under cyclic loading of a thin film bonded to substrate, wherein the method comprises producing an insonification pressure using microcavitation energy, subjecting the thin film to variations in insonification pressure levels, and determining an insonification pressure level at which the thin film may be subjected indefinitely without erosion whereby to indicate said endurance limit.

Another aspect of the invention includes an apparatus to test adherence of a thin film on a substrate comprising a source of insonification pressure that uses microcavitation, a test bed to support and position the substrate embodying the thin film at a region of insonification pressure, and a timer to measure elapse time from start of insonification pressure until observation of erosion. The apparatus preferably includes a level control to control the level of insonification pressure.

Other aspects of the invention will become apparent upon review of the following description taken in connection with the accompanying drawings.

DESCRIPTION OF ILLUSTRATIVE EMBODIMENT

In a method of testing thin film adhesion according to the present invention, a thin film on a substrate is subjected to controlled microcavitation. A test sample having a thin film bonded to substrate is placed at or near the focus region of desired cavitation of a cavitation-producing sound beam and the time required to achieve spot erosion provides a measure of adhesion strength. No erosion occurs if the insonification pressure amplitude is below a threshold value. At higher pressure amplitudes above a threshold value, cavitation intensity increases with pressure and spot erosion time decreases. A plot of erosion time versus pressure amplitude reveals a decreasing time versus insonification pressure. On this plot, the intercept of the plot with the pressure axis corresponds to the instantaneous erosion of the thin film spot, and thus to thin film adhesion strength. Further, the threshold value of the pressure at which there is no incipient erosion indicates infinite life of the thin film spot under cyclic loading and corresponds to the endurance limit, i.e., the fatigue strength, of the thin film deposited on the substrate.

The intercept of erosion time versus pressure amplitude on the pressure axis (which indicates tensile pressure) indicates the stress level corresponding to fracturing of the interfacial bond between the thin film and the substrate. Further, if the tension test was carried out under cyclic loading, then the endurance limit would be the highest amplitude of cyclic loading which the specimen can withstand indefinitely. Equivalently, the threshold pressure amplitude provides an upper estimate of the maximum stress value under which a thin film will endure indefinitely. The slop of the pressure-time plot indicated durability under loading conditions.

Thus the acoustic cavitation method quickly yields both the adhesion strength and the fatigue strength of the thin films.

The acoustic cavitation test herein described is practically nondestructive in the microelectronics because a wafer embodying thin film elements can be tested without any damage to the circuit (e.g., dies). The method and apparatus may be configured to confine the examination of thin film adherence to a specified portion of the wafer. With appropriately modified acoustics, the invention may be used to test larger spots or microspots. It can also be used with films of all thicknesses (several run to millimeter thick) and types (polymeric, paint-like, ink-like, metallics, platings, etc.) and substrates of all kinds (paper, glass, kevlar, composites, metals, and silicon wafers). It can cope with all samples as long as the thin film has at least a visual access. It can even be modified in certain circumstances to test interior films in enclosures (with fiber optic adaptations). The results are extremely easy to understand and interpret. They are consistent and quite repeatable.

Figure 1:
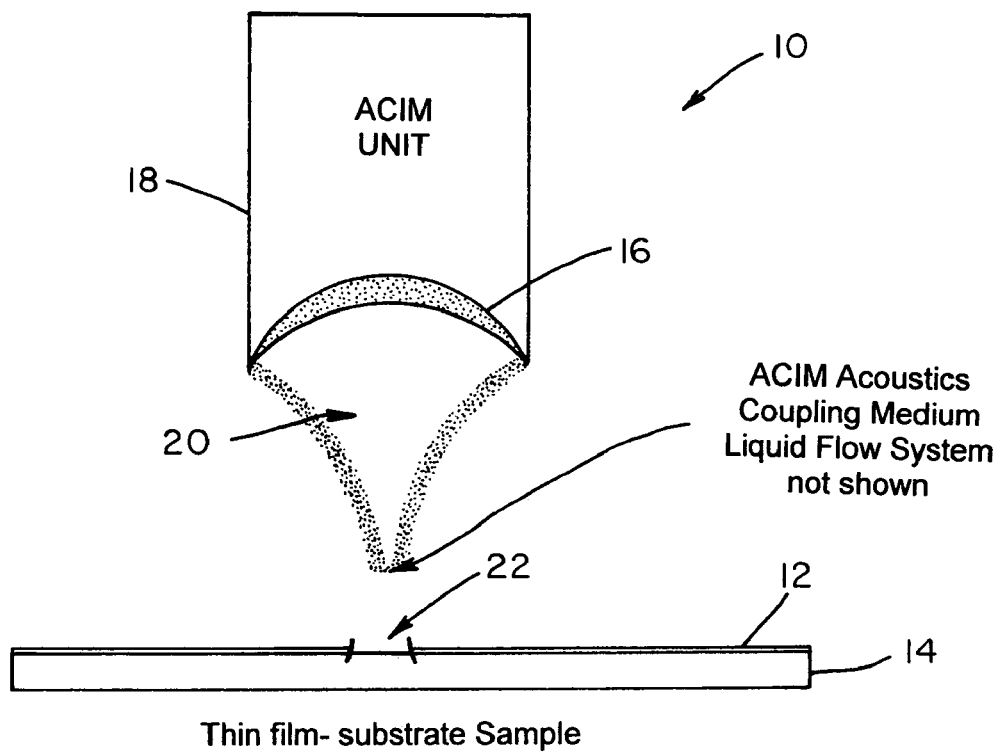
FIG. 1 illustrates one embodiment of an apparatus to subject a thin film to insonification pressure.

FIG. 1 depicts a simplified apparatus 10 for examining adhesion strength of a thin film 12 deposited on a substrate 14. Apparatus 10 comprises a microcavitation source comprising a transducer 16 mounted upon an air-backed housing 18 to generate a cavitation field 20 directed upon the thin film at a test location 22. Cavitation field 20 lies in liquid medium, e.g., water, which transfers acoustic energy from transducer 16 to the thin film 12. A suitable cavitation source is described in commonly-owned U.S. Pat. No. 6,395,096 entitled Single Transducer ACIM Method and Apparatus, incorporated herein.

Figure 2:
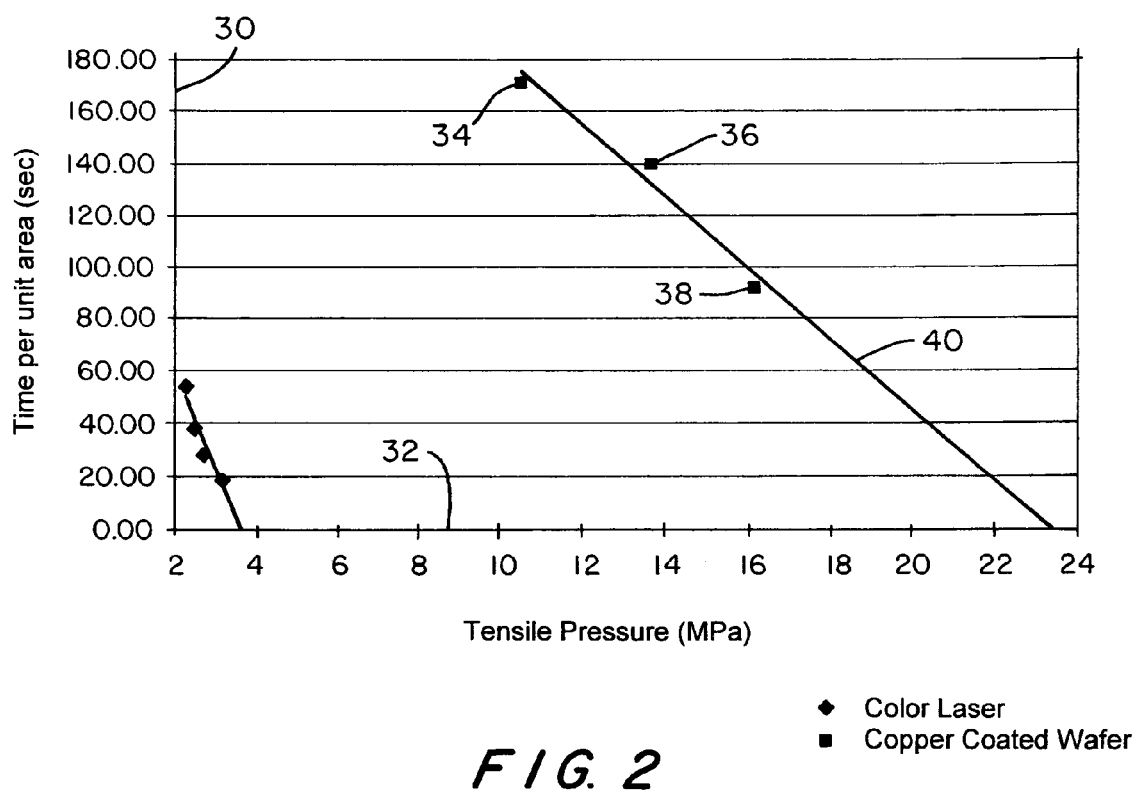
FIG. 2 shows a relationship between erosion time and insonification pressure.

FIG. 2 is a plot of erosion time versus insonification pressure. The time axis 30 is preferably normalized to indicated time per unit area. The pressure axis 32 indicates tensile pressure of insonification. Individual points 34, 36 and 38 indicate the time required to achieve spot erosion at a particular tensile pressure. Plot 40 is derived by interpolating a relationship based on a series of points 34, 36, and 38. No erosion occurs if the insonification pressure amplitude is below a threshold value. Extrapolating plot 40 to insect the pressure axis 32 provides an indication of adhesion strength. In particular, the intercept of plot 40 with the pressure axis 32 corresponds to the instantaneous erosion of a spot on the thin film, and thus to thin film adhesion strength. Thus, according to the invention, eroding a thin film using acoustic microcavitation provides an indication of adhesion strength.

What is claimed is:

1. A method of testing adherence of a thin film on a substrate, said method comprising:
   producing insonification pressure using microcavitation,
   subjecting the thin film to the insonification pressure,
   plotting erosion time of said thin film versus insonification pressure,
   determining a maximum instantaneous erosion pressure based on said plotting.

2. The method of claim 1, wherein said plotting includes observing a spot erosion of said thin film.

3. The method of claim 1, wherein said instantaneous erosion pressure is determined by extrapolating a plot of erosion time versus pressure.

* * * * *